US005196449A

United States Patent [19]

Magistretti et al.

[11] Patent Number: 5,196,449
[45] Date of Patent: Mar. 23, 1993

[54] METHODS AND PHARMACEUTICAL COMPOSITIONS FOR THE TREATMENT OF OPHTHALMIC DISEASES

[75] Inventors: Maria J. Magistretti; Marisa Conti; Giorgio Pifferi, all of Milan, Italy

[73] Assignee: IdB Holding SpA, Milan, Italy

[21] Appl. No.: 557,558

[22] Filed: Jun. 24, 1990

[30] Foreign Application Priority Data

Jul. 28, 1989 [GB] United Kingdom ............... 8917323

[51] Int. Cl.$^5$ ............................................. A61K 31/35
[52] U.S. Cl. ................................... 514/456; 514/912
[58] Field of Search ..................... 514/453, 456, 912

[56] References Cited

U.S. PATENT DOCUMENTS 4,925,871  5/1990  Gabetta et al. ..................... 514/453

OTHER PUBLICATIONS

Chem Abst. 94:71489t (1981) Kokai.

Primary Examiner—Frederick E. Waddell
Assistant Examiner—Zohreh A. Fay
Attorney, Agent, or Firm—Kirschstein, Ottinger, Israel & Schiffmiller

[57] ABSTRACT

The anthocyanidins pelargonidin and delphidin, have been found to possess novel and unexpected activity in the ophthalmic field, specifically that they are active in reducing the permeability of ciliary body vessels. According to one aspect of the present invention there is provided a method of reducing the hyperpermeability of the ciliary body ocular vessels in a subject which comprises administering to the subject an effective dose of pelargonidin or delphidin. The invention further provides the use of pelargonidin or delphidin in the manufacture of pharmaceutical compositions for carrying out the method of treatment referred to above.

6 Claims, No Drawings

METHODS AND PHARMACEUTICAL COMPOSITIONS FOR THE TREATMENT OF OPHTHALMIC DISEASES

BACKGROUND OF THE INVENTION

1. Field of the Invention

This invention relates to methods and pharmaceutical compositions for the treatment of ophthalmic diseases, and specifically to the use of selected anthocyanidins to elicit a specific ophthalmic pharmacological effect.

2. Description of Related Art

Anthocyanidins are known to have valuable pharamacological properties in treating peripheral vascular diseases. Thus our British Patent Nos. 1 589 294 and 1 595 531 describe and claim anthocyanidins which have cicatrizing, epithelium-regenerating, anti-inflammatory, vaso-protective, hypolipaemic, hypocholesterolaemic and hypoglycaemic activity. Owing to their low toxicity, these compounds are particularly useful for the prolonged treatment of patients with impaired peripheral circulation.

The glycosides of anthocyanidins (anthocyanosides) which are present as mixtures in extracts of certain fruits, have been described as being active in improving the visual function, particularly night vision (French Patent No. 1369 M, Jun. 25, 1962, Chibret). These compounds apparently accelerate the regeneration of rhodopsin, and thus facilitate adaptation to darkness.

SUMMARY OF THE INVENTION

We have now found that two of the anthocyanidins described in GB 1 589 294, namely pelargonidin and delphidin, have a novel and unexpected activity in the ophthalmic field, specifically that they are active in reducing the permeability of ciliary body vessels.

These blood vessels differ in their anatomic structure from the other ocular blood vessels and from the blood vessels of the general circulation and are involved in the regulation of endo-ocular pressure and of the blood-water barrier, and in the production of aqueous humor.

This newly-discovered activity of reducing the permeability of ciliary body vessels could not have been forecast from the known properties of anthocyanins or anthocyanosides.

The structure of pelargonidin and delphidin is as follows:

wherein
- in pelargonidin (Compound I) each R represents hydrogen,
- in delphinidin (Compound II) each R represents hydroxyl, and
- $X^-$ is a pharmaceutically acceptable anion, e.g. $Cl^-$.

The novel ophthalmic activity of these compounds has been established by various in vivo experiments in animal models.

Thus according to one aspect of the present invention there is provided a method of reducing the hyperpermeability of the ciliary body ocular vessels in a subject which comprises administering to the subject an effective dose of an anthocyanidin of formula wherein
- (I) each R represents hydrogen, or
- (II) each R represents hydroxy, and
- $X^-$ is a pharmaceutically acceptable anion, e.g. $Cl^-$.

The method of the invention is of particular utility in reducing the hyperpermeability of the ciliary body ocular vessels induced by injury or by harmful agents.

The invention further provides the use of an anthocyanidin of formula (I) and (II) above in the manufacture of pharmaceutical compositions for carrying out the methods of treatment referred to.

Various routes of administration may be used in carrying out the method of the invention. For example, the anthocyanidins may be administered orally or they may be administered locally to the eye.

DETAILED DESCRIPTION OF THE PREFERRED EMBODIMENTS

The specific pharmacological effects obtained according to the invention will now be described in more detail.

A. EFFECT ON THE PERMEABILITY OF THE HAEMATO-OPHTHALMIC BARRIER

The effect on the permeability of the haemato-ophthalmic barrier was measured by inducing an increase in the permeability of the vessels of the ciliary body, either by paracentesis or by instillation of sodium hydroxide into the conjunctival sac. The reduction in permeability induced by oral administration of the products under examination was then measured.

1. The Paracentesis Method (i) Acute Administration

The experiment was carried out on 80 New Zealand albino rabbits, average body weight 2.8 kg, divided into eight groups each of ten animals.

The vasal permeability was measured by the dye method: 1 ml of Evans Blue in a concentration of 0.5% was injected into the marginal vein of the auricle.

After 10 minutes the left eye was subjected to paracentesis and after 12 minutes a sample of aqueous humour was taken. The quantity of Evans Blue in the sampled aqueous humour was used to assess the permeability of the haemato-ophthalmic barrier. Immediately afterwards, compounds I and II were administered in doses of 100 or 200 mg/kg by stomach probe.

Two or four hours after administration, paracentesis was carried out on the right eye and after 12 minutes a sample of aqueous humour was taken.

The quantity of Evans Blue in the aqueous humour was evaluated by spectrophotometer reading at 623 nm.

(ii) Repeated Administration

The experiment was carried out on 20 New Zealand rabbits, average body weight 2.5 kg, using the same experimental technique as for acute administration.

The substances were administered in doses of 100 mg/kg os/day for seven days, and the effect on the permeability of the barrier was measured on the eighth day, 24 hours after the last administration.

Table 1 gives the results obtained with compounds I and II administered in a single dose of 100 or 200 mg/kg. The amount of dye coming out of the vessels of the ciliary body, two hours or four hours after administration, was reduced in a statistically significant manner. When the substances are repeatedly administered their effectiveness increases. The inhibition of the amount of dye emerging rose from 15% to 21-22% and was still statistically significant 24 hours after the last administration.

TABLE 1

Effect On The Permeability Of The Haemato-Ophthalmic Barrier Induced By Paracentesis In The Rabbit

| Substance | Dose mg/kg os | No. of Administrations | No. of Animals | Evans Blue (mcg/ml of aqueous humour) m ± s.d. | | | |
|---|---|---|---|---|---|---|---|
| | | | | Time 0 | 2 hours | 4 hours | 24 hours |
| Compound I | 100 | 1 | 10 | 41.2 ± 10.6 | 34.9 ± 8.5** (−15.4%) | | |
| | 100 | 1 | 10 | 55.5 ± 20.6 | | 46.9 ± 17.5** (−15.5%) | |
| | 200 | 1 | 10 | 50.5 ± 17.9 | 42.2 ± 15.0** (−16.4%) | | |
| | 200 | 1 | 10 | 53.1 ± 23.7 | | 44.8 ± 20.2** (−15.6%) | |
| | 100 | 7 | 10 | 56.9 ± 14.8 | | | 44.2 ± 11.7** (−22.4%) |
| Compound II | 100 | 1 | 10 | 48.3 ± 7.2 | 41.5 ± 7.9** (−14.1%) | | |
| | 100 | 1 | 10 | 53.6 ± 12.3 | | 45.6 ± 9.7** (−14.9%) | |
| | 200 | 1 | 10 | 53.1 ± 12.2 | 45.1 ± 10.3** (−15.1%) | | |
| | 200 | 1 | 10 | 54.1 ± 11.5 | | 45.9 ± 12.2** (−15.1%) | |
| | 100 | 7 | 10 | 53.7 ± 12.8 | | | 42.5 ± 13.3** (−20.8%) |

The brackets give the percentage variations relative to time 0
**$p < 0.01$ Student's "t" for paired data

2. Sodium Hydroxide Method

The experiment was carried out on 50 New Zealand rabbits, average body weight 2.2 kg. The substance was administered once a day for seven days in doses of 50 or 100 mg/kg. A control group was treated with tap water.

Thirty minutes after the last administration, 1 ml of a 0.5% solution of Evans Blue was administered in the marginal vein of the ear. After 30 minutes, inflammation of the eye tissue was produced by instilling two drops of 0.25N sodium hydroxide in the conjunctival sac. Two hours later the animal was anesthesized and a sample of aqueous humour was taken in order to measure the proportion of dye.

As Table 2 shows, compounds II and I both induced a dose-dependent reduction in the permeability of the vessels of the ciliary body caused by the irritating agent. The reduction following administration of 100 mg/kg was statistically significant compared with the controls.

TABLE 2

Effects Of Compounds I And II On The Permeability Of The Haemato-Ophthalmic Barrier Induced By NaOH In the Rabbit

| Substance | No. of Animals | Dose mg/kg/day os | Evans Blue mcg/ml m ± s.e. | Percentage Variation |
|---|---|---|---|---|
| Controls | 10 | — | 5.9 ± 0.6 | |
| Compound II | 10 | 50 | 5.1 ± 0.7 | −14 |
| | 10 | 100 | 3.2 ± 0.4* | −45 |
| Compound I | 10 | 50 | 5.8 ± 0.8 | −2 |
| | 10 | 100 | 3.5 ± 0.6* | −40 |

*$p < 0.05$ according to Student's "t" test

3. Corneal Lens Method

The experiment was carried out on 40 New Zealand rabbits, average body weight 2.5 kg, divided into three groups of ten animals each.

The vasal permeability was measured by the dye method: 1 ml of Evans Blue in a concentration of 0.5% was injected into the marginal vein of the ear. After 10 min a soft corneal lens embedded in a 2% solution of histamine hydrochloride was applied for 30 min to the left eye.

The left eye was subjected to paracentesis and a sample of aqueous humour was taken.

Immediately after, the substances were given by gavage at the dose of 100 mg/kg. Two or four hours after administration a lens embedded with histamine as described before was applied for 30 min on the right eye. Paracentesis was carried out and aqueous humor was taken.

The quantity of Evans Blue in the aqueous humor was evaluated as described in 1(i).

As Table 3 shows, compounds II and I both reduced permeability of the vessels of the ciliary body caused by histamine. The effects after 2 and 4 hours were statistically significant compared with the basal values.

TABLE 3

Effect on the Permeability of the Haemato-Ophthalmic Barrier Induced by Histamine

| Substance | Dose mg/kg/os | No. of animals | Evans Blue (mcg/ml of aqueous humour) $m \pm sd$ | | |
|---|---|---|---|---|---|
| | | | Time 0 | 2 hours | 4 hours |
| Compound II | 100 | 10 | 110.9 ± 32.7 | 82.0 ± 7.0*** (−25.3) | |
| | 100 | 10 | 100.6 ± 38.9 | | 68.8 ± 8.7*** (−31.7) |
| Compound I | 100 | 10 | 106.4 ± 29.5 | 86.2 ± 6.1** (−19.0) | |
| | 100 | 10 | 108.2 ± 16.4 | | 75.9 ± 10.3*** (−29.9) |

***$P < 0.001$
**$P < 0.01$ Student's "t" for paired data
In brackets the percentage variations relative to time 0.

B. ACUTE TOXICITY

This was tested on mice and rats after administration by stomach probe. Doses up to 6 g/kg of compounds I and II did not cause toxic symptoms or death. The LD 50 must therefore be above 6 g/kg.

C. OCULAR TOLERABILITY

The ocular tolerability of compounds I and II was measured in New Zealand rabbits on the anterior segment (conjunctiva, cornea, iris and crystalline lens) and on the posterior segment (vitreous humour and retina) after oral administration, local application and intra-ocular injection.

1. Oral Administration

Both products were administered by stomach probe, either in a single dose of 200 mg/kg or in repeated doses of 100 mg/kg for 7 days. Surveys were made before and 1, 2 and 4 hours after acute administration, on the third and seventh days after repeated administration and 5 days after suspension of treatment.

2. Local Application

The substances were instilled into the conjunctival sac in a quantity of 0.5 ml day of 1% aqueous suspensions for 30 days.

3. Intra-Ocular Injection

The substances were injected under anaesthesia into the front chamber at a concentration of 0.1%, after evacuation of the chamber. The ocular structures were examined by slit lamp, 1, 24 and 48 hours after injection.

Single or repeated oral administration of compounds I and II did not induce modifications in the conjunctive, cornea, iris, crystalline lens, vitrous humour or retina.

Local application was also perfectly tolerated.

After intracamerular injection, a blue coloration of the intracamerular structures was observed, together with hyperaemia of the conjunctiva and an inflammatory reaction which, in most cases, disappeared in 48 hours.

The intensity of the reactions was similar for both products.

On the basis of the test results for pharmacological and clinical activity, compounds I and II can be used in the treatment of conditions of increased capillary permeability following a noxious stimulus resulting in opening of intercellular junctions, break of blood aqueous barrier and leakage of seric proteins in the anterior chamber.

Such conditions of capillary fragility are frequent complications of diabetes. Therefore a direct action of compounds I and II on vasal permeability can improve ophthalmic affections in diabetic patients.

Various routes of administration may be used in carrying out the method of the invention. For example, the anthocyanidins may be administered orally or they may be administered locally to the eye.

The products according to the invention can be used in oral pharmaceutical forms such as tablets, capsules and sachets of granulate.

The following examples illustrate the invention without being limitative.

EXAMPLE 1 (Compound I, 100 mg, capsules)

Each capsule, size 2, contains:

| | |
|---|---|
| Compound I | 100 mg |
| Lactose | 138 mg |
| Methylcellulose | 4 mg |
| Sodium carboxymethylcellulose | 4 mg |
| Magnesium stearate | 2 mg |
| Talc | 2 mg |

EXAMPLE 2 (Compound II, 300 mg, capsules)

Each capsule, size 1, contains:

| | |
|---|---|
| Compound II | 300 mg |
| Methylcellulose | 6 mg |
| Sodium carboxymethylcellulose | 6 mg |
| Talc | 3 mg |
| Magnesium stearate | 3 mg |

EXAMPLE 3) (Compound II, 100 mg, tablets)

Each 160 mg tablet contains:

| | |
|---|---|
| Compound II | 100 mg |
| Methylcellulose | 2 mg |
| Sodium carboxymethylcellulose | 10 mg |
| Microgranular cellulose | 30 mg |
| Lactose | 12 mg |
| Talc | 3 mg |
| Magnesium stearate | 3 mg |

EXAMPLE 4) (Compound I, 300 mg, tablets)

Each 500 mg tablet contains:

| | |
|---|---|
| Compound I | 300 mg |
| Methylcellulose | 6 mg |
| Microgranular cellulose | 100 mg |
| Lactose | 70 mg |
| Sodium carboxymethylcellulose | 18 mg |
| Magnesium stearate | 3 mg |
| Talc | 3 mg |

EXAMPLE 5 (Compound I, 100 mg, granulate sachets)

Each 1 g sachet contains:

| | |
|---|---|
| Compound I | 100 mg |
| Mannitol | 400 mg |
| Ammonium glycyrrhizinate | 10 mg |
| Flavouring powder | 10 mg |
| Methylcellulose | 5 mg |
| Lactose | 475 mg |

EXAMPLE 6 (Compound II, 300 mg, granulate sachets)

-continued

| Each 1 g sachet contains: | |
|---|---|
| Compound II | 300 mg |
| Mannitol | 300 mg |
| Ammonium glycyrrhizinate | 10 mg |
| Flavouring powder | 10 mg |
| Methylcellulose | 5 mg |
| Lactose | 375 mg |

Example 7 (Compound II, 100 mg, lyophilized collyrium)

| Each "lyophilized" ampoule contains | |
|---|---|
| Compound II | 100 mg |
| Mannitol | 300 mg |

| Each "Solvent" ampoule contains: | |
|---|---|
| Hydroxypropylmethylcellulose | 40 mg |
| Benzalkonium chloride | 1 mg |
| Monobasic sodium phosphate | 82.8 mg |
| Dibasic sodium phosphate | 23.9 mg |
| Water for injection q.s. to | 10 ml |

We claim:

1. A method of reducing the hyperpermeability of the ciliary body ocular vessels in a subject which comprises administering to the subject a hyperpermeability-reducing effective dose of compound selected from the group consisting of anthocyanidins of formula

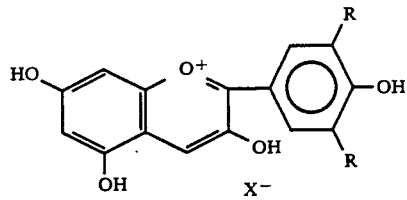

wherein
(I) each R represents hydrogen, or
(II) each R represents hydroxy, and
X represents one equivalent of a pharmaceutically acceptable anion.

2. A method according to claim 1 wherein the anthocyanidin is administered systemically.

3. A method according to claim 2 wherein the anthocyanidin is administered orally.

4. A method according to claim 1 wherein the anthocyanidin is administered locally to the eye.

5. A method according to claim 1 wherein the administration of anthocyanidin is effective in reducing the permeability of the haemato-ophthalmic barrier.

6. A method according to claim 1 wherein the subject is suffering from degenerative retinopathy, lack of retinal sensitivity, myopia or opthalmic complications of diabetes involving hyperpermeability of the ciliary body ocular vessel, or ophthalmic disorders secondary to vascular and metabolic diseases and involving hyperpermeability of the ciliary body ocular vessels.

* * * * *